US008501769B2

(12) United States Patent
Turner et al.

(10) Patent No.: US 8,501,769 B2
(45) Date of Patent: Aug. 6, 2013

(54) THIENOPYRIDYL COMPOUNDS THAT INHIBIT VANILLOID RECEPTOR SUBTYPE 1 (VR1) AND USES THEREOF

(75) Inventors: Sean T Turner, Mannheim (DE); Tammie K Jinkerson, Pleasant Prairie (IL); Arthur R. Gomtsyan, Vernon Hills, IL (US); Chih-hung Lee, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 288 days.

(21) Appl. No.: 12/968,666

(22) Filed: Dec. 15, 2010

(65) Prior Publication Data

US 2011/0082170 A1    Apr. 7, 2011

Related U.S. Application Data

(62) Division of application No. 11/293,012, filed on Dec. 2, 2005, now Pat. No. 7,875,627.

(60) Provisional application No. 60/633,957, filed on Dec. 7, 2004.

(51) Int. Cl.
*A01N 43/42* (2006.01)
*A61K 31/44* (2006.01)

(52) U.S. Cl.
USPC ............................................ 514/301

(58) Field of Classification Search
USPC ............................................ 514/301
See application file for complete search history.

(56) References Cited

U.S. PATENT DOCUMENTS

| | | | |
|---|---|---|---|
| 3,362,956 | A | 1/1968 | Archer |
| 3,845,065 | A | 10/1974 | Shen et al. |
| 4,839,365 | A | 6/1989 | Hirai et al. |
| 4,939,164 | A | 7/1990 | Wierzbicki et al. |
| 5,252,581 | A | 10/1993 | Effland et al. |

FOREIGN PATENT DOCUMENTS

| | | |
|---|---|---|
| DE | 257830 A1 | 6/1988 |
| EP | 292051 A2 | 11/1988 |
| EP | 581106 A1 | 2/1994 |
| EP | 1535922 A1 | 6/2005 |
| EP | 1277738 B1 | 3/2011 |
| FR | 2440738 A1 | 6/1980 |
| FR | 2564467 | 11/1985 |
| JP | 5202065 A | 8/1993 |
| JP | 25194198 A2 | 7/2005 |
| JP | 200645220 A | 2/2006 |
| JP | 2007526271 A | 9/2007 |
| WO | 9313664 A2 | 7/1993 |
| WO | WO9714681 A1 | 4/1997 |
| WO | WO0075145 A1 | 12/2000 |
| WO | 0183456 A1 | 11/2001 |
| WO | WO2004007495 A1 | 1/2004 |
| WO | WO2004096784 A1 | 11/2004 |
| WO | WO2005030706 A | 4/2005 |
| WO | WO2005070885 A | 8/2005 |
| WO | 2005085234 A2 | 9/2005 |
| WO | WO2005080391 A1 | 9/2005 |
| WO | WO2005085234 A2 | 9/2005 |
| WO | 2005105760 A1 | 11/2005 |

OTHER PUBLICATIONS

Szallasi et al., Am J Clin Pathol, vol. 118, (2002), pp. 110-121.*
Bohm N., et al., "Reactions of 4-oxo-4H-pyrido(3',2':4,5)thieno(3,2-d)-1,3-oxazines with Amines," Pharmazie, 1992, vol. 47 (12), pp. 897-901.
Brain M., et al., "A general method for the preparation of 2,3,5-trisubstitutedfuro[3,2-b]pyridines," Tetrahedron Letters, 2003, vol. 44, pp. 725-728.
Brugier D., et al., "Alpha-Substitution of Beta-Thienylcarbamates: Alkylation, Vinylation and Pd-Catalyzed Coupling Reactions," Tetrahedron, 2000, vol. 56 (19), pp. 2985-2993.
Caterina, M. J. et al., "Impaired Nociception and Pain Sensation in Mice Lacking the Capsaicin Receptor," Science, 2000, vol. 288, pp. 306-313.
Caterina, M. J. et al., "The Capsaicin Receptor: A Heat-Activated Ion Channel in the Pain Pathway," Nature, 1997, vol. 389 (6653), pp. 816-824.
Caterina, M. J. et al., "The Vanilloid Receptor: A Molecular Gateway to the Pain Pathway," Annual Review of Neuroscience, 2001, vol. 24, pp. 487-517.
Collier, H.O. et al., "The Abdominal Constriction Response and its Suppression by Analgesic Drugs in the Mouse," British Journal of Pharmacology and Chemotherapy, 1968, vol. 32 (2), pp. 295-310.
Davis, J. B. et al., "Vanilloid Receptor-1 is Essential for Inflammatory Thermal Hyperalgesia," Nature, 2000, vol. 405 (6783), pp. 183-187.
Dunn A.D., et al., "Novel Thienopyridines," Journal Fur Praktische Chemie, 1992, vol. 334 (6), pp. 483-486.
Fowler, C.J., "Intravesical Treatment of Overactive Bladder," Urology, 2000, vol. 55, pp. 60-64.
Frydman B., et al., "Pyrroles from Azaindoles a Synthesis of Porphobilinogen and Related Pyrroles," Journal of the American Chemical Society, 1969, vol. 91 (9), pp. 2338-2342.
Frydman B., et al., "Synthesis of 2-Aminomethylpyrroles and Related Lactams," Journal of Organic Chemistry, 1973, vol. 38 (10), pp. 1824-1831.

(Continued)

Primary Examiner — Niloofar Rahmani

(57) ABSTRACT

The present invention discloses fused thienopyridyl compounds of general formula (I)

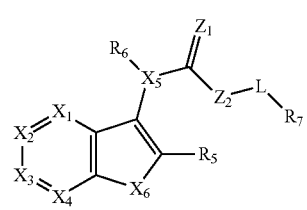

wherein $X_1$-$X_6$, $R_5$-$R_7$, $Z_1$ and L are as defined in the description. The resent invention also discloses a method for inhibiting the VR1 receptor in mammals using these compounds, a method for controlling pain, urinary incontinence, bladder overactivity, and inflammatory thermal hyperalgesia in mammals, and pharmaceutical compositions including those compounds.

5 Claims, No Drawings

OTHER PUBLICATIONS

Guerrera F., et al., "Synthesis of 1H-Imadazo [3',4':4,5] Thieno[2,3-bPyridines A New Ring System," Journal of Heterocyclic Chemistry, 1984, vol. 21, pp. 587-590.

Guerrera F., et al., "Synthesis of 3-Aminothieno-(2,3 -b)Pyridine Derivatives," IL Farmaco, 1984, vol. 31 (1), pp. 21-31.

Hayes, P. et al., "Cloning and Functional Expression of a Human Orthologue of Rat Vanilloid Receptor-1," Pain, 2000, vol. 88, pp. 205-215.

Klemm L.H. et al., "Chemistry of Thienopyridines XXV Comparative Mass Spectra of Some Amino and Acylamino Derivatives (1)," J.Heterocyclic.Chem, 1977, 299-303, vol. 14.

Nolano, M. et al., "Topical Capsaicin in Humans: Parallel Loss of Epidermal Nerve Fibers and Pain Sensation," Pain, 1999, vol. 81, pp. 135-145.

Pircio, A. W. et al., "A New Method for the Evaluation of Analgesic Activity Using Adjuvant-Induced Arthritis in the Rat," European Journal of Pharmacology, 1975, vol. 31 (2), pp. 207-215.

Santilli A.A., et al., "Thieno[2,3-d]pyrimidines 1 A New Method for the Preparation of Esters and Amides of Thieno [2,3-d] pyrimidine-6-carboxylic Acids," Journal of Heterocyclic Chemistry, 1971, vol. 8 (3), pp. 445-453.

Shiotani S., et al., "Furopyridines XV[1] Synthesis and Properties of Ethyl 2-(3-Furo[2,3-b]-, -[3,2-b]-, -[2,3-c]-, [3,2-c]pyridyl)acetate," Journal of Heterocyclic Chemistry, 1995, vol. 32, pp. 129-139.

Wagner G., et al., "Synthese von 3-alkyl-2-ammo-pyrido[3',2':4,5]thieno[3,2-d]pyrimidin-4 onen aus 3-Ethoxycarbonylamino-thieno[2,3-b]pyridin -2-carbonsäureethylestem and-2-carbonsaureamiden," Journal of Pharmazie, 1993, vol. 48 (2), pp. 95-99.

Berge, S. M. et al., "Pharmaceutical Salts," Journal of Pharmaceutical Sciences, 1977, vol. 66 (1), pp. 1-19.

Poste, G. et al., "Lipid Vesicles as Carriers for Introducing Biologically Active Materials into Cells," Methods in Cell Biology, 1976, vol. 14, pp. 33-71.

Briel, "Synthese von Thieno-Heterocyclen Ausgehend von Substituierten 5-Methylthio-thiophen-4-carbonitrilen," Pharmazie, 1998, 53(4), p. 227-231.

Kort, et al., "2 TRPV1 Antagonists: Clinical Setbacks and Prospects for Future Development," Abbott Laboratories, Neuroscience Disease Research, Abbott Park, IL, pp. 57-70, (2012).

Meyer et al., "Structure-Activity Studies for a Novel Series of Tricyclic Substituted Hexahydrobenz[e]isoindole Alpha(1A)...",J. Med. Chem., Apr. 20, 2000, 43(8), p. 1586-1603.

Moneam et al., "Synthesis of Pyridothienopyridines and Arylazothienopyridines," Phosphorus, Sulfur, and Silicon, 2003, 178, p. 2639-2651.

Parnes et al., "Novel 3-Aminothieno[2,2-b]pyridine Synthesis Via a Silicon-Directed Anionic Cyclization," Heterocycles, 2004, 63(10), p. 2199-2202.

Price et al., "Design of Novel N-(2,4-Dioxo-1,2,3,4-tetrahydro-thieno[3,2-d]pyrimidin-7-yl]-guanidines as Thymidine...", Bioorg. Med. Chem. Lett., 2003, 13, p. 107-110.

Reilly, et al., "Pharmacology of Modality-Specific Transient Receptor Potential Van...," Journal of Pharmacology and Experimental Therapeutics, (2012) 342(2), pp. 416-428.

Voight, et al., "Transient Receptor Potential Vanilloid-1 Antagonists: a Survey of Recent Patent Literature," Expert Opinion Ther. Patents, (2010), 20(9), pp. 1107-1122.

Wierzbicki, Michel et al., "Application a la Synthese de Quelques Thieno[2,3-b]pyrrole," Bulletin de la Societe Chimique de France, 1975, p. 1786-1792.

* cited by examiner

THIENOPYRIDYL COMPOUNDS THAT INHIBIT VANILLOID RECEPTOR SUBTYPE 1 (VR1) AND USES THEREOF

CROSS REFERENCE SECTION TO RELATED APPLICATIONS

This application is a divisional of U.S. application Ser. No. 11/293,012 filed on Dec. 2, 2005, which claims priority to U.S. Provisional Application Ser. No. 60/633,957 filed on Dec. 7, 2004, and are all incorporated by reference in their entirety.

FIELD OF THE INVENTION

The present invention relates to compounds of formula (I), which are useful for treating disorders caused by or exacerbated by vanilloid receptor activity, pharmaceutical compositions containing compounds of formula (I) and are useful in treating pain, bladder overactivity, and urinary incontinence.

BACKGROUND OF INVENTION

Nociceptors are primary sensory afferent (C and M fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents, which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel VR1 antagonists and have utility in treating pain, bladder overactivity, urinary incontinence and inflammatory thermal hyperalgesia.

SUMMARY OF THE PRESENT INVENTION

The present invention discloses fused thienopyridyl compounds, a method for inhibiting the VR1 receptor in mammals using these compounds, a method for controlling pain in mammals, and pharmaceutical compositions including those compounds. More particularly, the present invention is directed to compounds of formula (I)

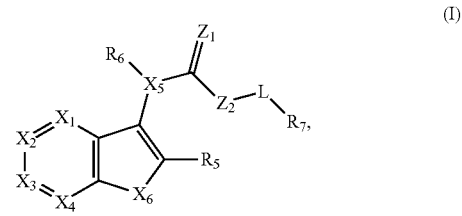

(I)

or a pharmaceutically acceptable salt or prodrug thereof, wherein
- - - is absent or a covalent bond;
$X_1$ is selected from N and $CR_1$;
$X_2$ is selected from N and $CR_2$;
$X_3$ is selected from N, $NR_3$ and $CR_3$;
$X_4$ is absent or selected from N and $CR_4$;
$X_5$ is selected from N and $CH_2$;
provided that at least one of $X_1$, $X_2$, $X_3$ and $X_4$ is N;
$X_6$ is selected from O, NH and S;
$Z_1$ is selected from O, NH and S;
$Z_2$ is absent or selected from NH and O;
L is selected from aryl, alkenylene, alkylene, alkynylene, cycloalkylene, heterocycle, —(CH$_2$)$_m$O(CH$_2$)$_n$—, —N(H)O—, and —NHNH— wherein the left end of —(CH$_2$)$_m$O(CH$_2$)$_n$— and —N(H)O— is attached to $Z_2$ and the right end is attached to $R_7$;
provided that when $Z_2$ is NH or O then L is other than —N(H)O— or —NHNH—;
m and n are each independently 1-6;
$R_1$, $R_3$ and $R_5$ are each independently selected from hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, (CF$_3$)$_2$(HO)C—, R$_B$S(O)$_2$R$_A$N—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl and $(Z_AZ_BN)$sulfonyl, wherein $Z_A$ and $Z_B$ are each independently selected from hydrogen, alkyl, alkylcarbonyl, formyl, aryl and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C$—, $R_BS(O)_2R_AN$—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl, $(ZAZ_BN)$sulfonyl, $(Z_AZ_BN)C(=NH)$—, $(Z_AZ_BN)C(=NCN)NH$—, and $(Z_AZ_BN)C(=NH)NH$—;

$R_A$ is selected from hydrogen and alkyl;

$R_A$ is selected from hydrogen and alkyl;

$R_B$ is selected from alkyl, aryl and arylalkyl;

$R_6$ is absent or selected from hydrogen and alkyl;

provided that $R_6$ is absent when $X_5$ is $CH_2$ and $R_6$ is selected from hydrogen and alkyl when $X_5$ is N; and $R_7$ is selected from hydrogen, aryl and heterocycle.

In another embodiment of the present invention there is disclosed a pharmaceutical composition comprising a therapeutically effective amount of a compound of formula (I) or a pharmaceutically acceptable salt thereof.

In a further embodiment of the present invention there is disclosed method of treating a disorder wherein the disorder is ameliorated by inhibiting vanilloid receptor subtype 1 (VR1) receptor in a host mammal in need of such treatment comprising administering a therapeutically effective amount of a compound of formula (I) or a pharmaceutically acceptable salt thereof.

DETAILED DESCRIPTION OF THE PRESENT INVENTION

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

(1) Embodiments

In the principal embodiment, compounds of formula (I) are disclosed

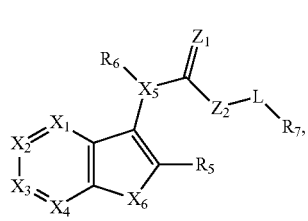

(I)

or a pharmaceutically acceptable salt or prodrug thereof, in which - - - is absent or is a covalent bond; $X_1$ is selected from N and $CR_1$; $X_2$ is selected from N and $CR_2$; $X_3$ is selected from N, $NR_3$ and $CR_3$; $X_4$ is absent or selected from N and $CR_4$; $X_5$ is selected from N and $CH_2$; provided that at least one of $X_1$, $X_2$, $X_3$ and $X_4$ is N; $X_6$ is selected from O, NH and S; $Z_1$ is selected from O, NH and S; $Z_2$ is absent or selected from NH and O; L is selected from aryl, alkenylene, alkylene, alkynylene, cycloalkylene, heterocycle, —$(CH_2)_mO(CH_2)_n$—, —$N(H)O$—, and —NHNH— wherein the left end of —$(CH_2)_mO(CH_2)_n$— and —$N(H)O$— is attached to $Z_2$ and the right end is attached to $R_7$; provided that when $Z_2$ is NH or O then L is other than —$N(H)O$— or —NHNH—; m and n are each independently 1-6; $R_1$, $R_3$ and $R_5$ are each independently selected from hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C$—, $R_BS(O)_2R_AN$—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl and $(Z_AZ_BN)$sulfonyl, wherein $Z_A$ and $Z_B$ are each independently selected from hydrogen, alkyl, alkylcarbonyl, formyl, aryl and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C$—, $R_BS(O)_2R_AN$—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl, $(ZAZ_BN)$sulfonyl, $(Z_AZ_BN)C(=NH)$—, $(Z_AZ_BN)C(=NCN)NH$—, and $(Z_AZ_BN)C(=NH)NH$—; $R_A$ is selected from hydrogen and alkyl; $R_B$ is selected from alkyl, aryl and arylalkyl; $R_6$ is absent or selected from hydrogen and alkyl; provided that $R_6$ is absent when $X_5$ is $CH_2$ and $R_6$ is selected from hydrogen and alkyl when $X_5$ is N; and $R_7$ is selected from hydrogen, aryl and heterocycle.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $R_1$, $R_2$, $R_4$, $R_5$, $R_6$, $R_7$, $X_5$, $X_6$, $Z_1$, $Z_2$, and L are as defined for formula (I) above.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_1$, $R_2$, $R_4$, $R_5$, $R_6$, and $R_7$ are as defined in formula (I).

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_5$ is a halogen; and $R_1$, $R_2$, $R_4$, $R_6$, and $R_7$ are as defined in formula (I).

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_5$ is alkyl; and $R_1$, $R_2$, $R_4$, $R_6$, and $R_7$ are as defined for formula (I) above.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_5$ is methyl, $R_7$ is aryl; and $R_1$, $R_2$, $R_4$ and $R_6$, are as defined for formula (I) above.

Another embodiment of the present invention comprises compounds of formula (I) in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_5$ is methyl, $R_7$ is phenyl substituted with 0, 1, 2, or 3 substituents independently selected from alkoxy, alkyl, alkylsulfonyl, cyano, haloalkoxy, haloalkyl, haloalkylthio, halogen, methylenedioxy, and $Z_AZ_BN$—; and $Z_A$, $Z_B$; and $R_1$, $R_2$, $R_4$ and $R_6$ are each hydrogen.

Another embodiment of the present invention comprises compounds of formula (I) in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is alkylene; $R_5$ is methyl, $R_7$ is naphthyl substituted with 0, 1, 2, or 3 substituents independently selected from alkoxy, alkyl, alkylsulfonyl, cyano, haloalkoxy, haloalkyl, haloalkylthio, halogen, methylenedioxy, and $Z_AZ_BN$—; and $Z_A$, $Z_B$ and $R_6$ are as defined for formula (I) above.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is aryl; $R_7$ is heterocycle, and $R_1$, $R_2$, $R_4$, $R_5$, $R_6$, are as defined in formula (I).

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is indanyl; $R_7$ is heterocycle, and $R_1$, $R_2$, $R_4$, $R_5$, $R_6$, are as defined in formula (I).

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is NH; L is heterocycle; and $R_1$, $R_2$, $R_4$, $R_5$, $R_6$, $R_7$, are as defined for formula (I) above.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is O; L is alkylene; and $R_1$, $R_2$, $R_4$, $R_5$, $R_6$, $R_7$, are as defined for formula (I) above.

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is O; L is alkylene; $R_7$ is aryl; and $R_1$, $R_2$, $R_4$, $R_5$, $R_6$, are as defined above for formula (I).

In another embodiment, compounds of formula (I) are disclosed, in which, - - - is a covalent bond; $X_1$ is $CR_1$; $X_2$ is $CR_2$; $X_3$ is N; $X_4$ is $CR_4$; $X_5$ is N; $X_6$ is S; $Z_1$ is O; $Z_2$ is O; L is alkylene; $R_7$ is phenyl substituted with 0, 1, 2, or 3 substituents independently selected from alkoxy, alkyl, alkylsulfonyl, cyano, haloalkoxy, haloalkyl, haloalkylthio, halogen, methylenedioxy, and $Z_AZ_BN$—; and $Z_A$, $Z_B$; and $R_1$, $R_2$, $R_4$, $R_5$, $R_6$, are as defined above for formula (I).

In yet another embodiment, compounds of formula (I) are disclosed, in which, - - - is a covalent bond; $X_1$ is $CR_1$; $X_2$ is N; $X_3$ is $CR_3$; $X_4$ is $CR_4$; $R_1$, $R_2$, $R_4$, $R_5$, $R_6$, $R_7$, $X_5$, $X_6$, $Z_1$, $Z_2$, and L are as defined above for formula (I).

The present invention also relates to a pharmaceutical composition comprising a therapeutically effective amount of a compound of formula (I) as defined above or a pharmaceutically acceptable salt thereof.

The present invention also relates to a method of treating a disorder that is ameliorated by inhibiting vanilloid receptor subtype 1 (VR1) receptor in a host mammal in need of such treatment comprising administering a therapeutically effective amount of a compound of formula (I) or a pharmaceutically acceptable salt thereof, where the disorder is selected from the group consisting of pain, urinary incontinence, bladder overactivity, and inflammatory thermal hyperalgesia.

Another embodiment of the present invention relates to a method for controlling pain in a host mammal in need of such treatment comprising administering a therapeutically effective amount of a compound of formula (I) or a pharmaceutically acceptable salt thereof.

Another embodiment of the present invention relates to a method of treating urinary incontinence in a host mammal in need of such treatment comprising administering a therapeutically effective amount of a compound of formula (I) or a pharmaceutically acceptable salt thereof.

Another embodiment of the present invention relates to a method of treating bladder overactivity in a host mammal in need of such treatment comprising administering a therapeutically effective amount of a compound of formula (I) or a pharmaceutically acceptable salt thereof.

Another embodiment of the present invention relates to a method of treating inflammatory thermal hyperalgesia in a host mammal in need of such treatment comprising administering a therapeutically effective amount of a compound of formula (I) or a pharmaceutically acceptable salt thereof.

(2) Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $Z_AZ_BN$—, ($Z_AZ_BN$)alkyl, ($Z_AZ_BN$)carbonyl, ($Z_AZ_BN$)carbonylalkyl, ($Z_AZ_BN$)sulfonyl, $R_BS(O)_2R_AN$—, $R_AOS(O)_2$— and $R_AS(O)_2$— wherein $R_A$ and $R_B$ are as defined herein. The aryl groups of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_AZ_B$, ($NZ_AZ_B$)alkyl, ($NZ_AZ_B$)carbonyl, ($NZ_AZ_B$)carbonylalkyl, ($NZ_AZ_B$)sulfonyl, —$NR_AS(O)_2R_B$, —$S(O)_2OR_A$ and —$S(O)_2R_A$ wherein $R_A$ and $R_B$ are as defined herein.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "amino" as used herein, means a $NH_2$ group.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —$O(CH_2)_2O$— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl(thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, arylalkyl, aryloxy, arylthio, carboxy, carboxyalkyl, cyano, cyanoalkyl, cycloalkyl, cycloalkylalkyl, formyl, formylalkyl, haloalkoxy, haloalkyl, haloalkylthio, halogen, heterocyclealkyl, heterocycleoxy, heterocyclethio, hydroxy, hydroxyalkyl, mercapto, mercaptoalkyl, nitro, oxo, —$NZ_AZ_B$, $(NZ_AZ_B)$alkyl, $(NZ_AZ_B)$carbonyl, $(NZ_AZ_B)$carbonylalkyl, $(NZ_AZ_B)$sulfonyl, —$NR_AS(O)_2R_B$, —$S(O)_2OR_A$ and —$S(O)_2R_A$ wherein $R_A$ and $R_B$ are as defined herein. The heterocycles of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_AZ_B$, $(NZ_AZ_B)$alkyl, $(NZ_AZ_B)$carbonyl, $(NZ_AZ_B)$carbonylalkyl, $(NZ_AZ_B)$sulfonyl, —$NR_AS(O)_2R_B$, —$S(O)_2OR_A$ and —$S(O)_2R_A$ wherein $R_A$ and $R_B$ are as defined herein.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —$OCH_2O$— group wherein the oxygen atoms of the methylenedioxy are attached to the parent molecular moiety through two adjacent carbon atoms.

The term "nitro" as used herein, means a —$NO_2$ group.

The term "$Z_AZ_BN$—" as used herein, means two groups, $Z_A$ and $Z_B$, which are appended to the parent molecular moiety through a nitrogen atom. $Z_A$ and $Z_B$ are each independently selected from hydrogen, alkyl, alkylcarbonyl, formyl, aryl and arylalkyl. Representative examples of $Z_AZ_BN$— include, but are not limited to, amino, methylamino, acetylamino, benzylamino, phenylamino, and acetylmethylamino.

The term "$(Z_AZ_BN)$alkyl" as used herein, means a $Z_AZ_BN$ group, as defined herein, appended to the parent molecular moiety through an alkyl group, as defined herein. Representative examples of $(Z_AZ_BN)$alkyl include, but are not limited to, aminomethyl, 2-(methylamino)ethyl, 2-(dimethylamino)ethyl and (ethylmethylamino)methyl.

The term "$(Z_AZ_BN)$carbonyl" as used herein, means a $Z_AZ_BN$ group, as defined herein, appended to the parent molecular moiety through a carbonyl group, as defined herein. Representative examples of $(Z_AZ_BN)$carbonyl include, but are not limited to, aminocarbonyl, (methylamino)carbonyl, (dimethylamino)carbonyl and (ethylmethylamino)carbonyl.

The term "$(Z_AZ_BN)$carbonylalkyl" as used herein, means a $(Z_AZ_BN)$carbonyl group, as defined herein, appended to the parent molecular moiety through an alkyl group, as defined herein. Representative examples of $(Z_AZ_BN)$carbonylalkyl include, but are not limited to, (aminocarbonyl)methyl, 2-((methylamino)carbonyl)ethyl and ((dimethylamino)carbonyl)methyl.

The term "($Z_AZ_BN$)sulfonyl" as used herein, means a $Z_AZ_BN$ group, as defined herein, appended to the parent molecular moiety through a sulfonyl group, as defined herein. Representative examples of ($Z_AZ_BN$)sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —S(O)$_2$— group.

(3) Preparation of Compounds of the Present Invention

The compounds and processes of the present invention will be better understood in connection with the following synthetic Schemes and Examples, which illustrate a means by which the compounds of the present invention can be prepared.

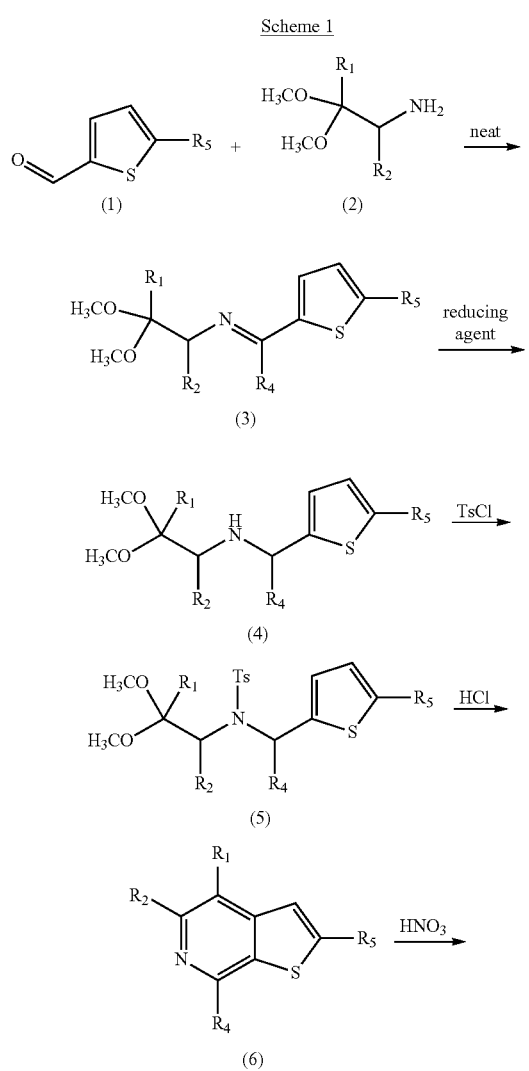

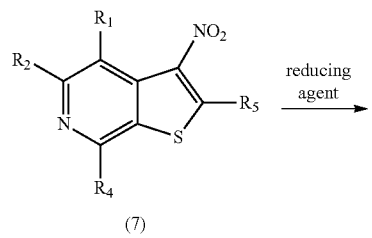

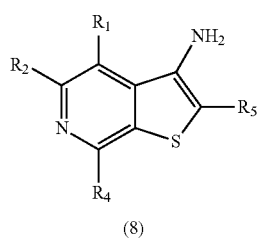

Amines of general formula (8), wherein $R_1$, $R_2$, $R_4$, and $R_5$ are defined in formula (I), may be prepared as described in Scheme 1. Aldehydes of general formula (1) can be treated with amines of general formula (2) to provide imines of general formula (3). Imines of general formula (3) can be treated with a reducing agent such as, but not limited to, 10% Pd/C under a hydrogen atmosphere (60 psi) in a solvent such as, but not limited to, methanol to provide amines of general formula (4). Amines of general formula (4) can be treated with an sulfonyl or acid chloride such as, but not limited to, p-toluenesulfonyl chloride in a solvent such as, but not limited to, ethyl acetate containing a base such as, but not limited to, triethylamine to provide a protected amine of general formula (5). Protected amines of general formula (5) can be treated with a concentrated acid such as, but not limited to, hydrochloric acid in a solvent such as, but not limited to, dioxane to provide cyclized thieno[2,3-c]pyridines of general formula (6). Thieno[2,3-c]pyridines of general formula (6) can be treated with a nitrating agent such as, but not limited to, nitric acid in a solvent of sulfuric acid to provide 3-nitro thieno[2,3-c]pyridines of general formula (7). 3-Nitro thieno[2,3-c]pyridines of general formula (7) can be treated with a reducing agent such as, but not limited to, Raney-Nickel in a solvent such as, but not limited to, methanol to provide 3-amino thieno[2,3-c]pyridines of general formula (8).

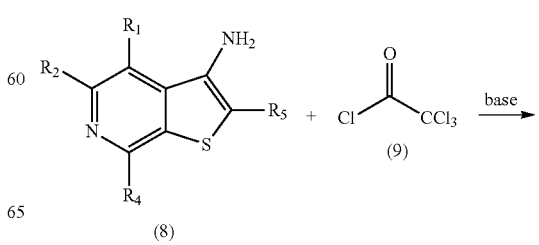

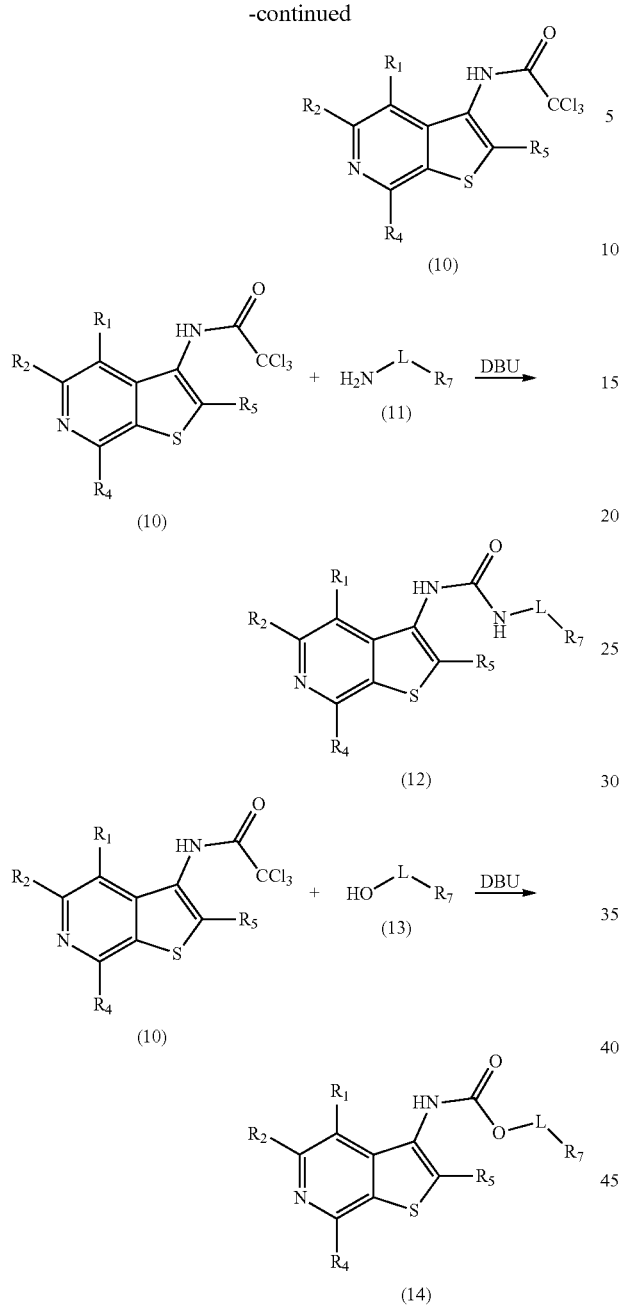

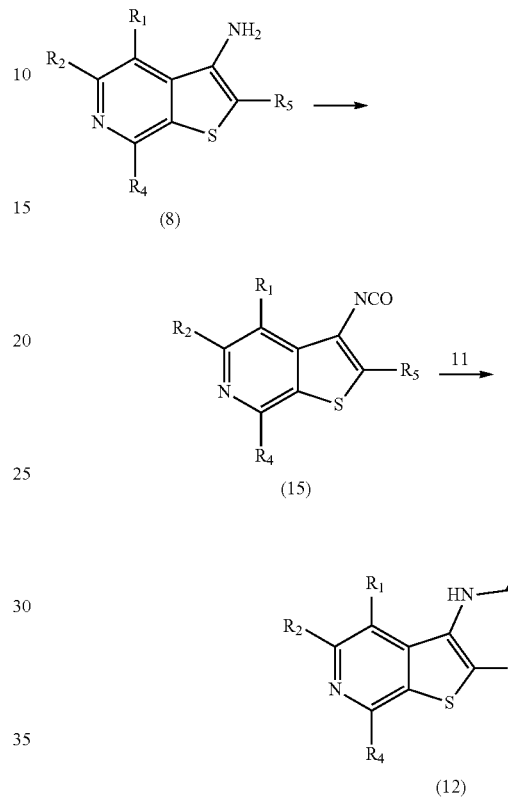

formula (13) and a non-nucleophilic base such as, but not limited to, DBU in a solvent such as, but not limited to, acetonitrile to provide carbamates of general formula (14).

Ureas of general formula (4), wherein $R_1$, $R_2$, $R_4$, $R_5$, $R_7$, and L are as defined in formula (I), may be prepared as described in Scheme 3. 3-Amino thieno[2,3-c]pyridines of general formula (8) can be treated with phosgene or triphosgene and DMAP in a solvent such as, but not limited to, dichloromethane to provide isocyanates of general formula (15). Isocyanates of general formula (15) can be treated with amines of general formula (11) in a solvent such as, but not limited to, toluene or THF or a combination thereof to provide ureas of general formula (12).

Ureas of general formula (12), wherein $R_1$, $R_2$, $R_4$, $R_5$, $R_7$, and L are as defined in formula (I), may be prepared as described in Scheme 2. 3-Amino thieno[2,3-c]pyridines of general formula (8), prepared using standard chemistry known to those in the art, can be treated with trichloroacetyl chloride and a base such as, but not limited to, triethylamine in a solvent such as dichloromethane to provide trichloroacetamides of general formula (10). Trichloroacetamides of general formula (10) can be treated with amines of general formula (9) and a non-nucleophilic base such as, but not limited to, DBU in a solvent such as, but not limited to, acetonitrile to provide ureas of general formula (12).

Carbamates of general formula (14), wherein $R_1$, $R_2$, $R_4$, $R_5$, $R_7$, and L are as defined in formula (I), may also be prepared as described in Scheme 2. Trichloroacetamides of general formula (10) can be treated with alcohols of general

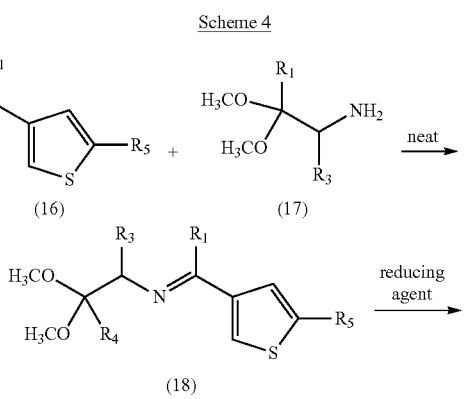

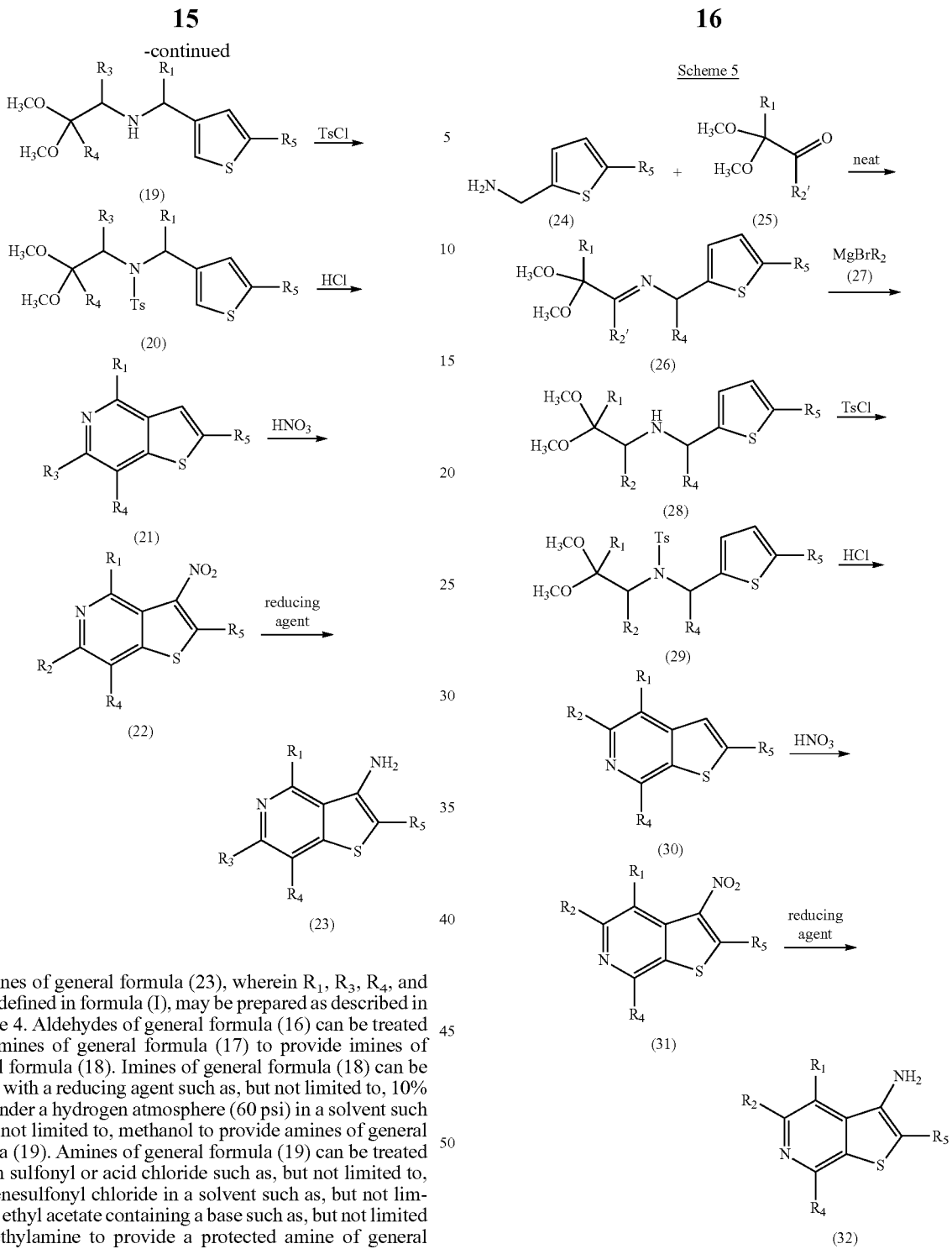

Amines of general formula (23), wherein $R_1$, $R_3$, $R_4$, and $R_5$ are defined in formula (I), may be prepared as described in Scheme 4. Aldehydes of general formula (16) can be treated with amines of general formula (17) to provide imines of general formula (18). Imines of general formula (18) can be treated with a reducing agent such as, but not limited to, 10% Pd/C under a hydrogen atmosphere (60 psi) in a solvent such as, but not limited to, methanol to provide amines of general formula (19). Amines of general formula (19) can be treated with an sulfonyl or acid chloride such as, but not limited to, p-toluenesulfonyl chloride in a solvent such as, but not limited to, ethyl acetate containing a base such as, but not limited to, triethylamine to provide a protected amine of general formula (20). Protected amines of general formula (20) can be treated with a concentrated acid such as, but not limited to, hydrochloric acid in a solvent such as, but not limited to, dioxane to provide cyclized thieno[3,2-c]pyridines of general formula (21). Thieno[3,2-c]pyridines of general formula (21) can be treated with a nitrating agent such as, but not limited to, nitric acid in a solvent of sulfuric acid to provide 3-nitro thieno[3,2-c]pyridines of general formula (22). 3-Nitro thieno[3,2-c]pyridines of general formula (22) can be treated with a reducing agent such as, but not limited to, Raney-Nickel in a solvent such as, but not limited to, methanol to provide 3-amino thieno[3,2-c]pyridines of general formula (23).

Amines of general formula (32), wherein $R_1$, $R_2$, $R_4$, and $R_5$ are defined in formula (1), may be prepared as described in Scheme 5. Amines of general formula (24) can be treated with aldehydes of general formula (25) to provide imines of general formula (26). Imines of general formula (26) can be treated with alkylating agents such as, but not limited to, Grignard reagents of general formula (27) in a solvent such as, but not limited to, THF to provide amines of general formula (28). Amines of general formula (28) can be treated with an sulfonyl or acid chloride such as, but not limited to, p-toluenesulfonyl chloride in a solvent such as, but not limited to, ethyl acetate containing a base such as, but not limited to, triethylamine to provide a protected amine of general formula (29). Protected amines of general formula (29) can be treated with a concentrated acid such as, but not limited to, hydrochloric acid in a solvent such as, but not limited to, dioxane to provide cyclized thieno[2,3-c]pyridines of general formula (30). Thieno[2,3-c]pyridines of general formula (30) can be treated with a nitrating agent such as, but not limited to, nitric acid in a solvent of sulfuric acid to provide 3-nitro thieno[2,3-c]pyridines of general formula (31). 3-Nitro thieno[2,3-c]pyridines of general formula (31) can be treated with a reducing agent such as, but not limited to, Raney-Nickel in a solvent such as, but not limited to, methanol to provide 3-amino thieno[2,3-c]pyridines of general formula (32).

pared using standard chemistry outlined in scheme 5, may be processed as described in Schemes 2-3 to provide ureas of general formula (35) and carbamates of general formula (36).

Ureas of general formula (33), wherein $R_1$, $R_3$, $R_4$, $R_5$, $R_7$, and L are as defined in formula (I), and carbamates of general formula (34), wherein $R_1$, $R_3$, $R_4$, $R_5$, $R_7$, and L are as defined in formula (I), may be prepared as described in Scheme 6. 3-Amino thieno[2,3-c]pyridine of general formula (23), prepared using standard chemistry outlined in scheme 4, may be processed as described in Schemes 2-3 to provide ureas of general formula (33) and carbamates of general formula (34).

Ureas of general formula (35), wherein $R_1$, $R_2$, $R_4$, $R_5$, $R_7$, and L are as defined in formula (I), and carbamates of general formula (36), wherein $R_1$, $R_2$, $R_4$, $R_5$, $R_7$, and L are as defined in formula (I), may be prepared as described in Scheme 6. 3-Amino thieno[2,3-c]pyridines of general formula (32), pre-

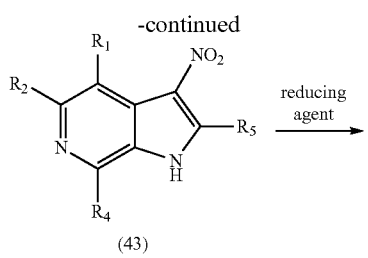

(43)

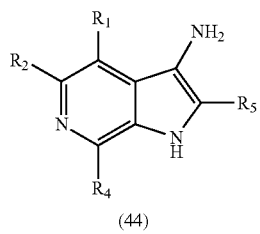

(44)

Amines of general formula (44), wherein $R_1$, $R_2$, $R_4$, and $R_5$ are defined in formula (I), may be prepared as described in Scheme 7. (3-Nitro-4-pyridyl)acetic esters of general formula (37) can be treated with dimethylformamide diethylacetals of general formula (38) in a solvent such as, but not limited to, DMF to provide (3-nitro-4-pyridyl)acetic ester dimethylaminovinyl derivatives of general formula (39). Dimethylaminovinyl derivatives of general formula (39) can treated with a reducing agent such as, but not limited to, 5% Pd/C under a hydrogen atmosphere (60 psi) in a solvent such as, but not limited to, ethanol to provide 3-ethoxycarbonyl-6-azaindoles of general formula (40). 3-Ethoxycarbonyl-6-azaindoles of general formula (40) can be treated with a base such as, but not limited to, potassium hydroxide in an aqueous solution to provide carboxylic acids of general formula (41). Carboxylic acids of general formula (41) can be thermally decarboxylated to provide 6-azaindoles of general formula (42). 6-Azaindoles of general formula (42) can be treated with a nitrating agent such as, but not limited to, fuming nitric acid to provide 3-nitro-6-azaindoles of general formula (43). 3-Nitro-6-azaindoles of general formula (43) can be treated to a reducing agent such as, but not limited to, Raney-Nickel in a solvent such as, but not limited to, methanol to provide 3-amino-6-azaindoles of general formula (44).

Scheme 8

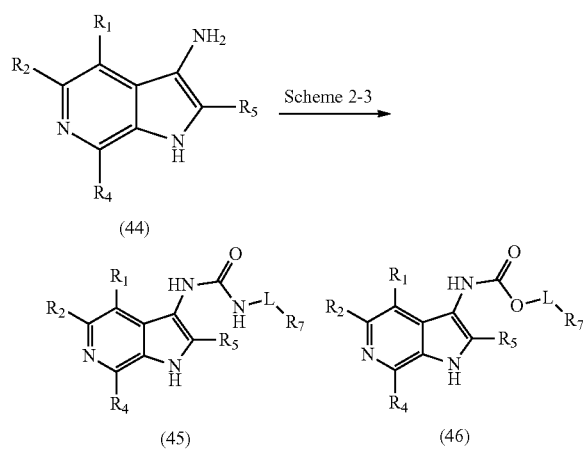

Ureas of general formula (45), wherein $R_1$, $R_2$, $R_4$, $R_5$, $R_7$, and L are as defined in formula (I), and carbamates of general formula (46), wherein $R_1$, $R_2$, $R_4$, $R_5$, $R_7$, and L are as defined in formula (I), may be prepared as described in Scheme 8. 3-Amino-6-azaindoles of general formula (44), prepared using standard chemistry outlined in scheme 7, may be processed as described in Schemes 2-3 to provide ureas of general formula (45) and carbamates of general formula (46).

(4) Examples

The following Examples are intended as an illustration of and not a limitation upon the scope of the invention as defined in the appended claims.

Example 1A (2,2-Dimethoxy-ethyl)-(5-methyl-thiophen-2-ylmethyl)-amine

Added aminoacetaldehyde dimethylacetal (27.5 g, 0.261 mol) to 5-methyl-2-thiophenecarboxaldehyde (25.0 g, 0.198 mol) and stirred at 0° C. for 30 min. Heated on rotavap for 30 min to remove excess aminoacetaldehyde. Obtained imine as a dark liquid (42.1 g, 100%).

Dissolved imine (42.1 g, 0.198 mol) in EtOH (170 mL) and added Pd—C (10%, 6.0 g). Reaction was shaken under hydrogen (60 psi) for 40 h. Reaction mixture was filtered and the collected catalyst washed with EtOH. Concentration in vacuo afforded the amine as a red liquid (42.1 g, 99%).

MS (ESI+) m/z 216 (M+H)$^+$; (ESI−) m/z 214 (M−H)$^+$; $^1$H NMR (DMSO-d$_6$) δ 2.38 (s, 3H), 2.68 (d, J 5.4, 1H), 3.25 (s, 6H), 3.79 (s, 2H), 4.64 (t, J 5.4, 2H), 6.60 (m, 1H), 6.70 (d, J 3.0, 1H.

Example 1B

N-(2,2-Dimethoxy-ethyl)-4-methyl-N-(5-methyl-thiophen-2-ylmethyl)-benzene sulfonamide Crude (2,2-dimethyoxy-ethyl)-(5-methyl-thiophen-2-ylmethyl)-amine (1) (43.41 g ~75% pure, 0.15 mol) was dissolved in EtOAc (150 mL) resulting in a yellow solution. Triethylamine (22 mL, 0.16 mol) was added. The mixture was cooled to 0° C. in ice bath. p-Toluenesulfonyl chloride (29.68 g, 0.16 mol) was added in small portions keeping the temperature below 15° C. After addition was complete the mixture was left in ice bath and allowed to slowly warm to room temperature and stirred for 20 hrs. The milky-yellow mixture was diluted with EtOAc (300 mL) and washed with water (2×400 mL), 1 M HCl (2×400 mL), water (1×400 mL), sat NaHCO$_3$ (1×400 mL), and brine (1×400 mL), dried (MgSO$_4$) and condensed to provide the title compound as a reddish-yellow liquid, 50.56 g. Product was not purified.

Example 1C

2-Methyl-thieno[2,3-c]pyridine

2-Methyl-thieno[2,3-c]pyridine (3): 76059-85: N-(2,2-Dimethoxy-ethyl)-4-methyl-N-(5-methyl-thiophen-2-ylmethyl)-benzenesulfonamide (2) (50.56 g crude) was dissolved in dioxane (250 mL) and conc. HCl (200 mL) was added cautiously. The dark red solution was heated at gentle reflux (105 to 110° C.) for 24 hours. The volume was reduced by approximately half, then diluted with ether (200 mL). The pH was adjusted to between 7 and 8 using 50% NaOH/H$_2$O and sat NaHCO$_3$ solution with cooling. More ether (400 mL) was added, the mixture was filtered to remove insoluble material and the phases separated. The organic phase was washed with water (2×350 mL), dried (MgSO$_4$) and condensed to dark red-brown oil. Purification was accomplished using Kugelrohr distillation (120 to 130° C.) to give 11.89 g of title compound as a pale yellow liquid.

MS (ESI+) m/z 150 (M+H)$^+$; (ESI−) m/z 148 (M−H)$^+$; $^1$H NMR (DMSO-d$_6$) δ 2.64 (s, 3H), 7.23 (s, 1H), 7.69 (d, J 6.4, 1H), 8.40 (d, J 6.4, 1H), 9.10 (s, 1H); Anal. Calcd for C$_8$H$_7$NS.0.9H$_2$O: C, 58.09; H, 5.36. Found: C, 58.01; H, 5.52.

Example 1D

2-Methyl-3-nitro-thieno[2,3-c]pyridine

2-Methyl-thieno[2,3-c]pyridine (5.51 g, 36.9 mmol) was dissolved in concentrated H$_2$SO$_4$ (20 mL) at 0° C. Concentrated HNO$_3$ (11.6 mL) was added dropwise over 15 min, followed by warming to RT. Stirred for 18 h at RT. The solution was poured over ice and adjusted pH to 7 with 50% NaOH/H$_2$O and sat NaHCO$_3$ solution. The solution was extracted with portions of CH$_2$Cl$_2$ (3×100 mL), dried (MgSO$_4$) and condensed to yield the title compound as a bright yellow solid (3.27 g, 46%).

MS (ESI+) m/z 195 (M+H)$^+$; (ESI−) m/z 193 (M−H)$^+$; $^1$H NMR (CDCl$_3$) δ 3.02 (s, 3H), 8.30 (d, J 5.8, 1H), 8.67 (d, J 5.8, 1H), 9.05 (s, 1H).

Example 1E 2,2,2-Trichloro-N-(2-methyl-thieno[2,3-c]pyridin-3-yl)-acetamide

Methyl-3-nitro-thieno[2,3-c]pyridine (2.05 g, 10.6 mmol) was dissolved in MeOH (250 mL) and added to a suspension of Raney-Nickel (20 g) in MeOH (100 mL). The reaction flask was flushed with H$_2$. After 3 hours at room temperature under a balloon of H$_2$ the reaction mixture was filtered and condensed to provide a yellow solid. This was then dissolved in DCM (100 mL) and triethylamine (1.6 mL, 11.5 mmol) was added. The solution was cooled to 0° C. in an ice bath. Trichloroacetyl chloride (1.3 mL, 11.6 mmol) was added dropwise. The solution was allowed to slowly warm to room temperature and stirred overnight (16 hrs), then concentrated to a yellow paste and partitioned between equal volumes of water and EtOAc (150 mL each). After separation the organic phase was washed with water (2×70 mL) and brine (1×70 mL), dried (MgSO$_4$) and condensed to provide the title compound as a tan solid (1.63 g, 42%). Used without purification.

General Coupling Procedure

The product from Example 1A (0.65 g, 2.25 mmol), DBU (0.85 g, 5.6 mmol) and 2-(3-fluorophenyl)ethylamine (0.35 g, 2.5 mmol) in acetonitrile (50 mL) were refluxed for 10 hours. The mixture was cooled, concentrated, diluted with ethyl acetate, washed twice with aqueous ammonium chloride and concentrated to dryness. The solid obtained was suspended in ethyl acetate and filtered to obtain 0.45 g (65%) of the title compound as a tan solid.

Example 1F 1-(4-Chloro-benzyl)-3-(2-methyl-thieno[2,3-c]pyridin-3-yl)-urea

The title compound was prepared using 4-chlorobenzylamine, the product from Example 1A, DBU and the procedure described in Example 1B. MS (ESI+) m/z 332 (M+H)$^+$; (ESI−) m/z 330 (M−H)$^+$; $^1$H NMR (DMSO-d$_6$) δ 2.62 (s, 3H), 4.31 (d, J 4.7, 2H), 7.25 (m, 2H), 7.37 (m, 4H), 8.01 (d, J 6.4, 1H), 8.64 (d, J 6.4, 1H), 8.91 (s, 1H), 9.62 (s, 1H); Anal. Calcd for C$_{16}$H$_{14}$ClN$_3$OS.1.25HCl: C, 50.92; H, 4.07. Found: C, 51.05; H, 3.93.

Example 2

1-(2,4-Dichloro-benzyl)-3-(2-methyl-thieno[2,3-c]pyridin-3-yl)-urea

The title compound was prepared using 2,4-dichlorobenzylamine, the product from Example 1A, DBU and the procedure described in Example 1B. MS (ESI+) m/z 366 (M+H)$^+$; (ESI−) m/z 364 (M−H)$^+$; $^1$H NMR (DMSO-d$_6$) δ 2.45 (s, 3H), 4.31 (d, J 6.0, 2H), 7.46 (m, 2H), 7.57 (m, 1H), 7.63 (m, 1H), 7.86 (d, J 6.4, 1H), 8.58 (d, J 6.4, 1H), 8.73 (s, 1H), 9.47 (s, 1H); Anal. Calcd for C$_{16}$H$_{13}$Cl$_2$N$_3$OS.1.1HCl: C, 47.29; H, 3.50; N, 10.34. Found: C, 47.61; H, 3.15; N, 10.20.

Example 3

1-(3,4-Dichloro-benzyl)-3-(2-methyl-thieno[2,3-c]pyridin-3-yl)-urea

The title compound was prepared using 3,4-dichlorobenzylamine, the product from Example 1A, DBU and the procedure described in Example 1B. MS (ESI+) m/z 366 (M+H)$^+$; (ESI−) m/z 364 (M−H)$^+$; $^1$H NMR (DMSO-d$_6$) δ 2.44 (s, 3H), 4.28 (d, J 6.1, 2H), 6.91 (t, J 6.1, 1H), 7.30 (d, J 8.2, 1H), 7.44 (d, J 5.2, 1H), 7.54 (s, 1H), 7.60 (d, J 8.2, 1H), 8.26 (s, 1H), 8.41 (d, J 5.2, 1H), 9.07 (s, 1H); Anal. Calcd for C$_{16}$H$_{13}$Cl$_2$N$_3$OS.1.1HCl: C, 47.29; H, 3.50; N, 10.34. Found: C, 47.48; H, 3.25; N, 10.16.

Example 4

1-(2-Methyl-thieno[2,3-c]pyridin-3-yl)-3-[1-methyl-1-(4-trifluoromethyl-phenyl)-ethyl]-urea The title compound was prepared using 1-methyl-1-(4-trifluoromethyl-phenyl)-ethylamine, the product from Example 1A, DBU and the procedure described in Example 1B. MS (ESI+) m/z 394 (M+H)$^+$; (ESI−) m/z 392 (M−H)$^+$; $^1$H NMR (DMSO-d$_6$) δ 1.63 (s, 6H), 2.53 (s, 3H), 7.08 (s, 1H), 7.66 (m, 2H), 7.75 (d, J 6.1, 1H), 8.29 (s, 1H), 8.56 (d, J 6.1, 1H), 9.42 (s, 1H); Anal. Calcd for C$_{16}$H$_{13}$Cl$_2$N$_3$OS.1CF$_3$CO$_2$H.0.5H$_2$O: C, 48.84; H, 3.90; N, 8.14. Found: C, 49.08; H, 3.76; N, 7.98.

Example 5

1-(2,3-Difluoro-4-trifluoromethyl-benzyl)-3-(2-methyl-thieno[2,3-c]pyridin-3-yl)-urea The title compound was prepared using 2,3-difluoro-4-trifluoromethylbenzylamine, the product from Example 1A, DBU and the procedure described in Example 1B. MS (ESI+) m/z 402 (M+H)$^+$; (ESI−) m/z 400 (M−H)$^+$; $^1$H NMR (DMSO-d$_6$) δ 2.62 (s, 3H), 4.48 (d, J 5.4, 2H), 7.41 (m, 2H), 7.66 (m, 1H), 8.01 (d, J 6.4, 1H), 8.65 (d, J 6.4, 1H), 9.07 (s, 1H), 9.62 (s, 1H); Anal. Calcd for C$_{17}$H$_{12}$F$_5$N$_3$OS.1.2HCl: C, 45.87; H, 2.99; N, 9.44. Found: C, 45.84; H, 2.84; N, 9.29.

Example 6

1-(2,4-Bis-trifluoromethyl-benzyl)-3-(2-methyl-thieno[2,3-c]pyridin-3-yl)-urea The title compound was prepared using 2,4-di(trifluoromethyl)benzylamine, the product from Example 1A, DBU and the procedure described in Example 1B.

MS (ESI+) m/z 434 (M+H)$^+$; (ESI−) m/z 432 (M−H)$^+$; $^1$H NMR (DMSO-d$_6$) δ 2.68 (s, 3H), 4.67 (d, J 5.8, 2H), 7.17 (t, J 6.1, 1H), 7.84 (m, 2H), 8.01 (s, 1H), 8.15 (d, J 7.8, 1H), 8.58 (d, J 6.1, 1H), 8.65 (s, 1H), 9.44 (s, 1H); Anal. Calcd for C$_{18}$H$_{13}$F$_6$N$_3$OS.0.85CF$_3$CO$_2$H: C, 44.62; H, 2.63; N, 7.92. Found: C, 44.92; H, 2.63; N, 7.56.

Example 7

1-(2-Chloro-4-trifluoromethyl-benzyl)-3-(2-methyl-thieno[2,3-c]pyridin-3-yl)-urea The title compound was prepared using 2-chloro-4-trifluoromethylbenzylamine, the product from Example 1A, DBU and the procedure described in Example 1B.

MS (ESI+) m/z 400 (M+H)$^+$; (ESI−) m/z 398 (M−H)$^+$; $^1$H NMR (DMSO-d$_6$) δ 2.63 (s, 3H), 4.45 (d, J 5.8, 2H), 7.30 (t, J 6.1, 1H), 7.64 (d, J 8.1, 1H), 7.80 (m, 2H), 7.86 (s, 1H), 7.99 (d, J 6.4, 1H), 8.64 (d, J 6.4, 1H), 8.95 (s, 1H), 9.59 (s, 1H); Anal. Calcd for C$_{17}$H$_{13}$ClF$_3$N$_3$OS.0.6CF$_3$CO$_2$H: C, 46.69; H, 2.93; N, 8.97. Found: C, 46.64; H, 3.15; N, 9.02.

Example 8

1-(4-Bromo-3-methyl-benzyl)-3-(2-methyl-thieno[2,3-c]pyridin-3-yl)-urea

The title compound was prepared using 4-bromo-3-methylbenzylamine, the product from Example 1A, DBU and the procedure described in Example 1B.

MS (ESI+) m/z 366 (M+H)$^+$; (ESI−) m/z 364 (M−H)$^+$; $^1$H NMR (DMSO-d$_6$) δ 2.34 (s, 3H), 2.55 (s, 3H), 4.24 (d, J 5.8, 2H), 6.93 (t, J 6.1, 1H), 7.07 (m, 1H), 7.27 (s, 1H), 7.54 (d, J 8.1, 1H), 7.77 (d, J 6.1, 1H), 8.37 (s, 1H), 8.56 (d, J 6.1, 1H), 9.41 (s, 1H); Anal. Calcd for C$_{17}$H$_{16}$BrN$_3$OS.CF$_3$CO$_2$H: C, 45.25; H, 3.40; N, 8.33. Found: C, 45.22; H, 3.46; N, 8.35.

Example 9

1-(4-trifluoromethoxy-benzyl)-3-(2-methyl-thieno[2,3-c]pyridin-3-yl)-urea

The title compound was prepared using 4-trifluoromethoxybenzylamine, the product from Example 1A, DBU and the procedure described in Example 1B.

$^1$H NMR (DMSO-d$_6$) δ 2.44 (s, 3H), 4.31 (d, J 4.7, 2H), 6.86 (t, J 6.0, 1H), 7.33 (d, J 7.9, 2H), 7.43 (m, 3H), 8.17 (s, 1H), 8.40 (d, J 5.5, 1H), 9.05 (s, 1H).

Example 10

1-(3-trifluoromethylbenzyl)-3-(2-methyl-thieno[2,3-c]pyridin-3-yl)-urea

The title compound was prepared using 3-trifluoromethylbenzylamine, the product from Example 1A, DBU and the procedure described in Example 1B.

$^1$H NMR (DMSO-d$_6$) δ 2.44 (s, 3H), 4.37 (d, J 4.7, 2H), 6.94 (t, J 6.0, 1H), 7.42 (d, J 7.9, 1H), 7.59 (m, 4H), 8.24 (s, 1H), 8.39 (d, J 5.5, 1H), 9.05 (s, 1H).

Example 11

1-(3-Trifluoromethoxybenzyl)-3-(2-methyl-thieno[2,3-c]pyridin-3-yl)-urea

The title compound was prepared using 3-trifluoromethoxybenzylamine, the product from Example 1A, DBU and the procedure described in Example 1B.

$^1$H NMR (DMSO-d$_6$) δ 2.43 (s, 3H), 4.32 (d, J 5.9, 2H), 6.99 (t, J 6.0, 1H), 7.22 (d, J 7.2, 1H), 7.26 (s, 1H), 7.32 (d, J 8.0, 1H), 7.45 (m, 2H), 8.19 (s, 1H), 8.39 (d, J 5.5, 1H), 9.05 (s, 1H).

Example 12

(2-Methyl-thieno[2,3-c]pyridin-3-yl)-carbamic acid 4-trifluoromethyl-benzyl ester The title compound was prepared using 4-trifluoromethoxybenzyl alcohol, the product from Example 1A, DBU and the procedure described in Example 1B. $^1$H NMR (DMSO-d$_6$) δ 2.45 (s, 3H), 5.27 (d, J 4.7, 2H), 6.86 (t, J 6.0, 1H), 7.33 (d, J 7.9, 2H), 7.43 (m, 3H), 8.17 (s, 1H), 8.40 (d, J 5.5, 1H), 9.05 (s, 1H).

Example 13

(2-Methyl-thieno[2,3-c]pyridin-3-yl)-carbamic acid 4-trifluoromethoxy-benzyl ester The title compound was prepared using 4-trifluoromethoxybenzyl alcohol, the product from Example 1A, DBU and the procedure described in Example 1B. $^1$H NMR (DMSO-d$_6$) δ 2.44 (s, 3H), 5.19 (s, 2H), 6.86 (t, J 6.0, 1H), 7.42 (m, 3H), 7.57 (m, 2H), 8.40 (d, J 5.5, 1H), 9.08 (s, 1H), 9.45 (s, 1H).

Example 14

(2-Methyl-thieno[2,3-c]pyridin-3-yl)-carbamic acid 4-trifluoromethylsulfanyl-benzyl ester The title compound was prepared using 4-trifluoromethylsulfanyl-benzyl_alcohol, the product from Example 1A, DBU and the procedure described in Example 1B.

$^1$H NMR (DMSO-d$_6$) δ 2.45 (s, 3H), 5.24 (s, 2H), 7.46 (d, J 5.5, 1H), 7.61 (m, 2H), 7.76 (m, 2H), 8.40 (d, J 5.5, 1H), 9.08 (s, 1H), 9.50 (s, 1H).

Example 15

1-Benzyl-3-(2-methyl-thieno[2,3-c]pyridin-3-yl)-urea

The title compound was prepared using benzylamine, the product from Example 1A, DBU and the procedure described in Example 1B. MS (ESI+) m/z 298 (M+H)$^+$; (ESI−) m/z 396 (M−H)$^+$; $^1$H NMR (DMSO-d$_6$) δ 2.57 (s, 3H), 4.31 (d, J 4.7, 2H), 7.03 (t, J 6.0, 1H), 7.26 (m, 1H), 7.33 (m, 5H), 7.84 (d, J 6.2, 1H), 8.48 (s, 1H), 8.58 (d, J 5.5, 1H), 9.48 (s, 1H).

Example 16

1-(2-Methyl-benzyl)-3-(2-methyl-thieno[2,3-c]pyridin-3-yl)-urea

The title compound was prepared using 2-methylbenzylamine, the product from Example 1A, DBU and the procedure described in Example 1B. MS (ESI+) m/z 312 (M+H)$^+$; (ESI−) m/z 310 (M−H)$^+$; $^1$H NMR (DMSO-d$_6$) δ 2.30 (s, 3H), 2.57 (s, 3H), 4.30 (d, J 4.7, 2H), 6.87 (t, J 6.0, 1H), 7.18 (m, 3H), 7.29 (d, 1H), 7.83 (d, J 6.2, 1H), 8.39 (s, 1H), 8.58 (d, J 5.5, 1H), 9.46 (s, 1H).

Example 17

1-(3-Methyl-benzyl)-3-(2-methyl-thieno[2,3-c]pyridin-3-yl)-urea

The title compound was prepared using 3-methylbenzylamine, the product from Example 1A, DBU and the procedure described in Example 1B. MS (ESI+) m/z 312 (M+H)$^+$; (ESI−) m/z 310 (M−H)$^+$; $^1$H NMR (DMSO-d$_6$) δ 2.31 (s, 3H), 2.57 (s, 3H), 4.28 (d, J 4.7, 2H), 6.95 (t, J 6.0, 1H), 7.15 (m, 3H), 7.24 (m, 1H), 7.81 (d, J 6.2, 1H), 8.41 (s, 1H), 8.58 (d, J 5.5, 1H), 9.45 (s, 1H).

Example 18

1-(4-Methyl-benzyl)-3-(2-methyl-thieno[2,3-c]pyridin-3-yl)-urea

The title compound was prepared using 4-methylbenzylamine, the product from Example 1A, DBU and the procedure described in Example 1B. MS (ESI+) m/z 312 (M+H)$^+$; (ESI−) m/z 310 (M−H)$^+$; $^1$H NMR (DMSO-d$_6$) δ 2.29 (s, 3H), 2.56 (s, 3H), 4.26 (d, J 4.7, 2H), 6.94 (t, J 6.0, 1H), 7.15 (d, 2H), 7.20 (d, 2H), 7.81 (d, J 6.2, 1H), 8.41 (s, 1H), 8.58 (d, J 5.5, 1H), 9.45 (s, 1H).

Example 19

1-(3-Fluoro-5-trifluoromethyl-benzyl)-3-(2-methyl-thieno[2,3-c]pyridin-3-yl)-urea The title compound was prepared using 3-fluoro-5-trifluoromethyl-benzylamine, the product from Example 1A, DBU and the procedure described in Example 1B.
MS (ESI+) m/z 384 (M+H)$^+$; (ESI−) m/z 382 (M−H)$^+$; $^1$H NMR (DMSO-d$_6$) δ 2.55 (s, 3H), 4.40 (d, J 4.7, 2H), 7.12 (t, J 6.0, 1H), 7.45 (d, 1H), 7.54 (s, 1H), 7.78 (d, J 6.2, 1H), 8.53 (s, 1H), 8.57 (d, J 5.5, 1H), 9.43 (s, 1H).

Example 20

1-(4-Methoxy-benzyl)-3-(2-methyl-thieno[2,3-c]pyridin-3-yl)-urea

The title compound was prepared using 4-methoxybenzylamine, the product from Example 1A, DBU and the procedure described in Example 1B. MS (ESI+) m/z 328 (M+H)$^+$; (ESI−) m/z 326 (M−H)$^+$; $^1$H NMR (DMSO-d$_6$) δ 2.29 (s, 3H), 2.56 (s, 3H), 4.26 (d, J 4.7, 2H), 6.94 (t, J 6.0, 1H), 7.15 (d, 2H), 7.20 (d, 2H), 7.81 (d, J 6.2, 1H), 8.41 (s, 1H), 8.58 (d, J 5.5, 1H), 9.45 (s, 1H).

Example 21

1-(2-Fluorobenzyl)-3-(2-methyl-thieno[2,3-c]pyridin-3-yl)-urea

The title compound was prepared using 2-fluorobenzylamine, the product from Example 1A, DBU and the procedure described in Example 1B. MS (ESI+) m/z 316 (M+H)$^+$; $^1$H NMR (DMSO-d$_6$) δ 2.56 (s, 3H), 4.36 (d, J 4.7, 2H), 6.87 (t, J 6.0, 1H), 7.19 (m, 1H), 7.26 (m, 1H), 7.40 (m, 1H), 7.66 (m, 1H), 7.80 (d, J 6.2, 1H), 8.41 (s, 1H), 8.56 (d, J 5.5, 1H), 9.44 (s, 1H).

Example 22

1-(3-Fluorobenzyl)-3-(2-methyl-thieno[2,3-c]pyridin-3-yl)-urea

The title compound was prepared using 3-fluorobenzylamine, the product from Example 1A, DBU and the procedure described in Example 1B. MS (ESI+) m/z 316 (M+H)$^+$; (ESI−) m/z 314 (M−H)$^+$; $^1$H NMR (DMSO-d$_6$) δ 2.57 (s, 3H), 4.33 (d, J 4.7, 2H), 7.05-7.18 (m, 4H), 7.38 (m, 1H), 7.84 (d, J 6.2, 1H), 8.53 (s, 1H), 8.59 (d, J 5.5, 1H), 9.48 (s, 1H).

Example 23

1-(4-Fluorobenzyl)-3-(2-methyl-thieno[2,3-c]pyridin-3-yl)-urea

The title compound was prepared using 4-fluorobenzylamine, the product from Example 1A, DBU and the procedure described in Example 1B. MS (ESI+) m/z 316 (M+H)$^+$; (ESI−) m/z 314 (M−H)$^+$; $^1$H NMR (DMSO-d$_6$) δ 2.56 (s, 3H), 4.29 (d, J 4.7, 2H), 7.04 (t, J 6.0, 1H), 7.17 (m, 2H), 7.36 (m, 2H), 7.83 (d, J 6.2, 1H), 8.49 (s, 1H), 8.59 (d, J 5.5, 1H), 9.48 (s, 1H).

Example 24

1-(2-Chlorobenzyl)-3-(2-methyl-thieno[2,3-c]pyridin-3-yl)-urea

The title compound was prepared using 2-chlorobenzylamine, the product from Example 1A, DBU and the procedure described in Example 1B. MS (ESI+) m/z 332 (M+H)$^+$; (ESI−) m/z 330 (M−H)$^+$; $^1$H NMR (DMSO-d$_6$) δ 2.58 (s, 3H), 4.39 (d, J 4.7, 2H), 7.05 (t, J 6.0, 1H), 7.31 (d, J 6.2, 1H), 7.37 (d, J 6.2, 1H), 7.44 (m, 2H), 7.83 (d, J 6.2, 1H), 8.57 (s, 1H), 8.58 (d, J 5.5, 1H), 9.46 (s, 1H).

Example 25

1-(3-Chlorobenzyl)-3-(2-methyl-thieno[2,3-c]pyridin-3-yl)-urea

The title compound was prepared using 3-chlorobenzylamine, the product from Example 1A, DBU and the procedure described in Example 1B. MS (ESI+) m/z 332 (M+H)$^+$; (ESI−) m/z 330 (M−H)$^+$; $^1$H NMR (DMSO-d$_6$) δ 2.56 (s, 3H), 4.33 (d, J 4.7, 2H), 7.03 (t, J 6.0, 1H), 7.29 (m, 2H), 7.37 (m, 1H), 7.49 (m, 1H), 7.80 (d, J 6.2, 1H), 8.45 (s, 1H), 8.57 (d, J 5.5, 1H), 9.44 (s, 1H).

Example 26

1-(2-Bromobenzyl)-3-(2-methyl-thieno[2,3-c]pyridin-3-yl)-urea

The title compound was prepared using 2-bromobenzylamine, the product from Example 1A, DBU and the procedure described in Example 1B. MS (ESI+) m/z 378 (M+H)$^+$; (ESI−) m/z 376 (M−H)$^+$; $^1$H NMR (DMSO-d$_6$) δ 2.58 (s, 3H), 4.35 (d, J 4.7, 2H), 7.08 (t, J 5.6, 1H), 7.23 (m, 1H), 7.42 (d, J 4.1, 1H), 7.62 (d, J 7.8, 1H), 7.83 (d, J 6.0, 1H), 8.58 (d, J 5.9, 1H), 8.62 (s, 1H), 9.46 (s, 1H).

Example 27

1-(3-Bromobenzyl)-3-(2-methyl-thieno[2,3-c]pyridin-3-yl)-urea

The title compound was prepared using 3-bromobenzylamine, the product from Example 1A, DBU and the procedure described in Example 1B. MS (ESI+) m/z 378 (M+H)$^+$; (ESI−) m/z 376 (M−H)$^+$; $^1$H NMR (DMSO-d$_6$) δ 2.56 (s, 3H), 4.30 (d, J 4.7, 2H), 7.01 (t, J 5.6, 1H), 7.32 (d, J 5.3, 1H), 7.45 (m, 1H), 7.51 (s, 1H), 7.80 (d, J 6.0, 1H), 8.43 (s, 1H), 8.58 (d, J 5.9, 1H), 9.44 (s, 1H).

Example 28

11-(2-Methyl-thieno[2,3-c]pyridin-3yl)-3-naphthalen-1-ylmethylurea

The title compound was prepared using naphthalene-1-ylmethylamine, the product from Example 1A, DBU and the procedure described in Example 1B.

MS (ESI+) m/z 348 (M+H)$^+$; (ESI−) m/z 346 (M−H)$^+$; $^1$H NMR (DMSO-d$_6$) δ 2.57 (s, 3H), 4.79 (d, J 5.6, 2H), 7.01 (t, J 5.6, 1H), 7.32 (m, 5H), 7.83 (d, J 6.0, 1H), 7.89 (m, 1H), 7.97 (d, J 7.5, 1H), 8.37 (s, 1H), 8.58 (d, J 5.9, 1H), 9.46 (s, 1H).

Example 29

1-(2,3-Dimethylbenzyl)-3-(2-methyl-thieno[2,3-c]pyridin-3-yl)-urea

The title compound was prepared using 2,3-dimethylbenzylamine, the product from Example 1A, DBU and the procedure described in Example 1B. MS (ESI+) m/z 326 (M+H)$^+$; (ESI−) m/z 324 (M−H)$^+$; $^1$H NMR (DMSO-d$_6$) δ 2.19 (s, 3H), 2.26 (s, 3H), 2.54 (s, 3H), 4.30 (d, J 4.7, 2H), 6.72 (t, J 6.0, 1H), 7.08 (m, 2H), 7.14 (m, 1H), 7.74 (d, J 5.9, 1H), 8.22 (s, 1H), 8.54 (d, J 5.5, 1H), 9.38 (s, 1H).

Example 30

1-(2,5-Dimethylbenzyl)-3-(2-methyl-thieno[2,3-c]pyridin-3-yl)-urea

The title compound was prepared using 2,5-dimethylbenzylamine, the product from Example 1A, DBU and the procedure described in Example 1B. MS (ESI+) m/z 326 (M+H)$^+$; (ESI−) m/z 324 (M−H)$^+$; $^1$H NMR (DMSO-d$_6$) δ 2.24 (s, 3H), 2.27 (s, 3H), 2.56 (s, 3H), 4.25 (d, J 4.7, 2H), 6.76 (t, J 6.0, 1H), 6.97 (m, 1H), 7.15 (m, 2H), 7.77 (d, J 5.7, 1H), 8.27 (s, 1H), 8.56 (d, J 6.0, 1H), 9.40 (s, 1H).

Example 31

1-(3,4-Dimethylbenzyl-1)-3-(2-methyl-thieno[2,3-c]pyridin-3-yl)-urea

The title compound was prepared using 3,4-dimethylbenzylamine, the product from Example 1A, DBU and the procedure described in Example 1B. MS (ESI+) m/z 326 (M+H)$^+$; (ESI−) m/z 324 (M−H)$^+$; $^1$H NMR (DMSO-d$_6$) δ 2.20 (s, 3H), 2.22 (s, 3H), 2.55 (s, 3H), 4.23 (d, J 5.9, 2H), 6.76 (t, J 5.9, 1H), 7.02 (m, 1H), 7.09 (m, 2H), 7.77 (d, J 6.2, 1H), 8.31 (s, 1H), 8.56 (d, J 5.9, 1H), 9.41 (s, 1H).

Example 32

1-(2-Methyl-thieno[2,3-c]pyridin-3-yl)-3-(5-piperidin-1-yl-indan-1-yl)-urea

The title compound was prepared using 5-piperidin-1-yl-indan-1-ylamine, the product from Example 1A, DBU and the procedure described in Example 1B.

MS (ESI+) m/z 407 (M+H)$^+$; (ESI−) m/z 405 (M−H)$^+$; $^1$H NMR (DMSO-d$_6$) δ 1.55 (m, 7H), 1.73 (m, 1H), 2.50 (s, 3H), 2.73 (m, 1H), 2.85 (m, 1H), 3.09 (m, 4H), 5.08 (d, J 7.4, 1H), 6.53 (d, J 8.1, 1H), 6.80 (m, 2H), 7.14 (d, J 8.8, 1H), 7.49 (d, J 5.4, 1H), 7.92 (s, 1H), 8.43 (d, J 5.4, 1H), 9.06 (s, 1H).

(5) Determination of Biological Activity (a) In Vitro Data—Determination of Inhibition Potencies Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate) (without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. *Pain* Vol 88, pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 μg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR)(Molecular Devices, Sunnyvale, Calif.). Cells were grown to confluence in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10th second time mark of the experimental run. Then, after a 3-minute time delay, 50 µL of the capsaicin solution was added at the 190-second time mark (0.05 µM final concentration) (final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190th second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from 5000 nM to 0.1 nM. In a preferred range, twelve (12) compounds tested had $IC_{50s}$ from 500 nM to 0.1 nM. In a more preferred range, six (6) compounds tested had $IC_{50s}$ from 100 nM to 0.1 nM.

(b) In Vivo Data—Determination of Antinociceptive Effect

Experiments were performed on 400 adult male 129 J mice (Jackson laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., *Br. J. Pharmacol. Chemother. Vol.* 32 pages 295-310 (1968). Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing causally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The other antinociceptive test used was Complete Freund's Adjuvant-induced Thermal Hyperalgesia (CFA) assay described in Pircio et al. *Eur J. Pharmacol. Vol.* 31 (2) pages 207-215 (1975). Chronic inflammatory hyperalgesia was induced in one group of rats following the injection of complete Freund's adjuvant (CFA, 50%, 150 µL) into the plantar surface of the right hindpaw 48 hours prior to testing. Thermal nociceptive thresholds were measured in three different groups of rats. The $ED_{50s}$ were determined based on the oral administration. The $ED_{50}$ values for two compounds tested were 30 and 10 mmol/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, inflammatory thermal hyperalgesia, bladder overactivity, and urinary incontinence.

Compounds of the present invention, including but not limited to those specified in the examples, can be used to treat pain as demonstrated by Nolano, M. et al., *Pain Vol.* 81 pages 135-145 (1999); Caterina, M. J. and Julius, D., *Annu. Rev. Neurosci. Vol.* 24, pages 487-517 (2001); Caterina, M. J. et al., *Science Vol.* 288 pages 306-313 (2000); Caterina, M. J. et al., *Nature Vol.* 389, pages 816-824 (1997).

Compounds of the present invention, including but not limited to those specified in the examples, can be used to treat bladder overactivity and/or urinary incontinence as demonstrated by Fowler, C. *Urology Vol.* 55 pages 60-64 (2000).

Compounds of the present invention, including but not limited to those specified in the examples, can be used to treat inflammatory thermal hyperalgesia as demonstrated by Davis, J. et al., *Nature Vol.* 405 pages 183-187 (2000).

The present invention also provides pharmaceutical compositions that comprise compounds of the present invention. The pharmaceutical compositions comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), Poste et al., Chapter 4, p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s), which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (*J. Pharmaceutical Sciences Vol.* 66, pages 1 et seq (1977). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

Compounds of the present invention were named by ACD/ChemSketch version 5.0 (developed by Advanced Chemistry Development, Inc., Toronto, ON, Canada) or were given names, which appeared to be consistent with ACD nomenclature.

Abbreviations

Abbreviations which have been used in the descriptions of the Schemes and the Examples that follow are: DBU for 1,8-diazabicyclo[5.4.0] undec-7-ene; DCC for 1,3-dicyclohexylcarbodiimide; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; HPLC high pressure liquid chromatography; NBS for N-bromosuccinimide; psi for pounds per square inch; and THF for tetrahydrofuran.

We claim:

1. A method of treating a disorder selected from the group consisting of pain, urinary incontinence, and bladder overactivity in a host mammal in need of such treatment comprising administering to the host mammal a therapeutically effective amount of a compound of formula (I):

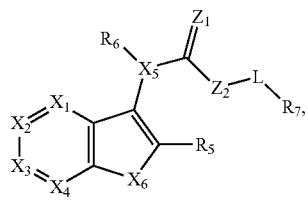

or a pharmaceutically acceptable salt thereof, wherein - - - is absent or a covalent bond;

$X_1$ is $CR_1$;
$X_2$ is $CR_2$;
$X_3$ is N;
$X_4$ is $CR_4$;
$X_5$ is selected from N and $CH_2$;
$X_6$ is selected from O, NH and S;
$Z_1$ is selected from O, NH and S;
$Z_2$ is absent or selected from NH and O;
L is selected from aryl, alkenylene, alkylene, alkynylene, cycloalkylene, heterocycle, —$(CH_2)_mO(CH_2)_n$—, —N(H)O—, and —NHNH— wherein the left end of —$(CH_2)_mO(CH_2)_n$— and —N(H)O— is attached to $Z_2$ and the right end is attached to $R_7$;
provided that when $Z_2$ is NH or O then L is other than —N(H)O— or —NHNH—;
m and n are each independently 1-6;
$R_1$, $R_3$ and $R_5$ are each independently selected from hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C$—, $R_BS(O)_2R_AN$—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl and $(Z_AZ_BN)$sulfonyl, wherein $Z_A$ and $Z_B$ are each independently selected from hydrogen, alkyl, alkylcarbonyl, formyl, aryl and arylalkyl;
$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, amines, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C$—, $R_BS(O)_2R_AN$—, $R_AOS(O)_2$—, $R_B$—$S(O)_2$—, $Z_AZ_BN$—, $(Z_AZ_BN)$alkyl, $(Z_AZ_BN)$carbonyl, $(Z_AZ_BN)$alkylcarbonyl, $(ZAZ_BN)$sulfonyl, $(Z_AZ_BN)C(=NH)$—, $(Z_AZ_BN)C(=NCN)NH$—, and $(Z_AZ_BN)C(=NH)NH$—;
$R_A$ is selected from hydrogen and alkyl;
$R_B$ is selected from alkyl, aryl and arylalkyl;
$R_6$ is absent or selected from hydrogen and alkyl;
provided that $R_6$ is absent when $X_5$ is $CH_2$ and $R_6$ is selected from hydrogen and alkyl when $X_5$ is N; and
$R_7$ is selected from hydrogen, aryl and heterocycle.

2. The method of claim 1 wherein the disorder is pain.

3. The method of claim 1 wherein the disorder is urinary incontinence.

4. The method of claim 1 wherein the disorder is bladder overactivity.

5. The method of claim 1 wherein the compound of formula (I) is selected from the group consisting of:
1-(4-chloro-benzyl)-3-(2-methyl-thieno[2,3-c]pyridin-3-yl)-urea;
1-(2,4-dichloro-benzyl)-3-(2-methyl-thieno[2,3-c]pyridin-3-yl)-urea;
1-(3,4-dichloro-benzyl)-3-(2-methyl-thieno[2,3-c]pyridin-3-yl)-urea;
1-(2-methyl-thieno[2,3-c]pyridin-3-yl)-3-[1-methyl-1-(4-trifluoromethylphenyl)-ethyl]-urea;
1-(2,3-difluoro-4-trifluoromethyl-benzyl)-3-(2-methyl-thieno[2,3-c]pyridin-3-yl)-urea;
1-(2,4-bis-trifluoromethyl-benzyl)-3-(2-methyl-thieno[2,3-c]pyridin-3-yl)-urea;
1-(2-chloro-4-trifluoromethyl-benzyl)-3-(2-methyl-thieno[2,3-c]pyridin-3-yl)-urea;
1-(4-bromo-3-methyl-benzyl)-3-(2-methyl-thieno[2,3-c]pyridin-3-yl)-urea;
1-(4-trifluoromethoxy-benzyl)-3-(2-methyl-thieno[2,3-c]pyridin-3-yl)-urea;
1-(3-trifluoromethylbenzyl)-3-(2-methyl-thieno[2,3-c]pyridin-3-yl)-urea;
1-(3-trifluoromethoxybenzyl)-3-(2-methyl-thieno[2,3-c]pyridin-3-yl)-urea;
(2-methyl-thieno[2,3-c]pyridin-3-yl)-carbamic acid 4-trifluoromethyl-benzyl ester;
(2-methyl-thieno[2,3-c]pyridin-3-yl)-carbamic acid 4-trifluoromethoxy-benzyl ester;
(2-methyl-thieno[2,3-c]pyridin-3-yl)-carbamic acid 4-trifluoromethylsulfanyl-benzyl ester;
1-benzyl-3-(2-methyl-thieno[2,3-c]pyridin-3-yl)-urea;
1-(2-methyl-benzyl)-3-(2-methyl-thieno[2,3-c]pyridin-3-yl)-urea;
1-(3-methyl-benzyl)-3-(2-methyl-thieno[2,3-c]pyridin-3-yl)-urea;
1-(4-methyl-benzyl)-3-(2-methyl-thieno[2,3-c]pyridin-3-yl)-urea;
1-(3-Fluoro-5-trifluoromethyl-benzyl)-3-(2-methyl-thieno[2,3-c]pyridin-3-yl)-urea;
1-(4-methoxy-benzyl)-3-(2-methyl-thieno[2,3-c]pyridin-3-yl)-urea;
1-(2-fluorobenzyl)-3-(2-methyl-thieno[2,3-c]pyridin-3-yl)-urea;
1-(3-fluorobenzyl)-3-(2-methyl-thieno[2,3-c]pyridin-3-yl)-urea;
1-(4-fluorobenzyl)-3-(2-methyl-thieno[2,3-c]pyridin-3-yl)-urea;
1-(2-chlorobenzyl)-3-(2-methyl-thieno[2,3-c]pyridin-3-yl)-urea;
1-(3-chlorobenzyl)-3-(2-methyl-thieno[2,3-c]pyridin-3-yl)-urea;

1-(2-bromobenzyl)-3-(2-methyl-thieno[2,3-c]pyridin-3-yl)-urea;
1-(3-bromobenzyl)-3-(2-methyl-thieno[2,3-c]pyridin-3-yl)-urea;
1-(2-methyl-thieno[2,3-c]pyridin-3-yl)-3-naphthalen-1-ylmethylurea;
1-(2,3-dimethylbenzyl)-3-(2-methyl-thieno[2,3-c]pyridin-3-yl)-urea;
1-(2,5-dimethylbenzyl)-3-(2-methyl-thieno[2,3-c]pyridin-3-yl)-urea;
1-(3,4-dimethylbenzyl)-3-(2-methyl-thieno[2,3-c]pyridin-3-yl)-urea; and
1-(2-methyl-thieno[2,3-c]pyridin-3-yl)-3-(5-piperidin-1-yl-indan-1-yl)-urea.

* * * * *